(12) United States Patent
Ali et al.

(10) Patent No.: US 11,435,288 B1
(45) Date of Patent: Sep. 6, 2022

(54) METHOD FOR DETECTING MERCURY WITH PYRENE FUNCTIONALIZED SILICA NANOPARTICLES

(71) Applicant: KING FAHD UNIVERSITY OF PETROLEUM AND MINERALS, Dhahran (SA)

(72) Inventors: Shahid Ali, Dhahran (SA); Muhammad Mansha, Dhahran (SA); Safyan Akram Khan, Dhahran (SA); Nadeem Baig, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 17/745,358

(22) Filed: May 16, 2022

(51) Int. Cl.
*G01N 21/64* (2006.01)
*G01N 33/2028* (2019.01)
*G01N 21/17* (2006.01)

(52) U.S. Cl.
CPC ..... *G01N 21/6428* (2013.01); *G01N 33/2028* (2019.01); *G01N 2021/174* (2013.01)

(58) Field of Classification Search
CPC ........... G01N 21/6428; G01N 33/2028; G01N 2021/174
See application file for complete search history.

(56) References Cited

FOREIGN PATENT DOCUMENTS

| CN | 103364376 A | 10/2013 |
|---|---|---|
| CN | 113092423 A | 7/2021 |
| ES | 2 302 462 | 6/2009 |
| IN | 201611003054 | 1/2018 |
| KR | 10-1665046 | 10/2016 |

OTHER PUBLICATIONS

Ali S, Mansha M, Baig N, Khan SA. Cost-Effective and Selective Fluorescent Chemosensor (Pyr-NH@SiO2 NPs) for Mercury Detection in Seawater. Nanomaterials (Basel). Apr. 7, 2022;12(8):1249. doi: 10.3390/nano12081249. PMID: 35457957; PMCID: PMC9024866. (Year: 2022).*

DNA-Capped Mesoporous Silica Nanoparticles as an Ion-Responsive Release System to Determine the Presence of Mercury in Aqueous Solutions Yunfei Zhang, Quan Yuan, Tao Chen, Xiaobing Zhang, Yan Chen, and Weihong Tan Analytical Chemistry 2012 84 (4), 1956-1962 (Year: 2012).*

(Continued)

*Primary Examiner* — David P Porta
*Assistant Examiner* — Gisselle M Gutierrez
(74) *Attorney, Agent, or Firm* — Oblon, McClelland, Maier & Neustadt, L.L.P.

(57) ABSTRACT

A method for detecting mercury ($Hg^{2+}$) ions in an aqueous solution is described. The method includes contacting the aqueous solution with a chemosensor to form a mixture; and monitoring a change in a fluorescence emission profile of the chemosensor in the mixture to determine the presence or absence of $Hg^{2+}$ ions in the aqueous solution. The chemosensor includes pyrene silica nanoparticles where at least one pyrene is bonded to a surface of a silica nanoparticle through an amide bond with a formula of, pyrene-C(=O)NHR-silica nanoparticle, and where R is an alkyl chain.

20 Claims, 14 Drawing Sheets

(56) References Cited

OTHER PUBLICATIONS

Zeynep Munteha Sahin et al., Highly sensitive and reusable mercury (II) sensor based on fluorescence quenching of pyrene moiety in polyacrylamide-based cryogel, Sensors and Actuators B: Chemical, vol. 242, 2017, pp. 362-368, ISSN 0925-4005, https://doi.org/10.1016/j.snb.2016.11.048. (Year: 2017).*
Wang, et al.; Colloids and Surfaces A: Physiochemical and Engineering Aspects, vol. 637; Mar. 20, 2022; Abstract Only; 3 Pages.
Wang, et al.; Fluorescent and colorimetric magnetic microspheres as nanosensors for Hg2+ in aqueous solution prepared by a sol-gel grafting reaction and host-guest interaction; Nanoscales, Issue 11; 2013; Abstract Only; 6 Pages.
Radhakrishnan, et al.; Magnetic core-shell fibrous silica functionalized with pyrene derivative for highly sensitive and selective detection of Hg(II) ion; Journal of Dispersion Science and Technology, vol. 40, Issue 9; Aug. 2, 2019; Abstract Only; 5 Pages.
Sahin, et al.; Highly sensitive and reusable mercury (II) sensor based on fluorescence quenching of pyrene moiety in polyacrylamide-based cryogel; Sensors and Actuators B: Chemical, 242; pp. 362-368; Nov. 10, 2016; 7 Pages.

\* cited by examiner

METHOD FOR DETECTING MERCURY WITH PYRENE FUNCTIONALIZED SILICA NANOPARTICLES

BACKGROUND

Technical Field

The present disclosure is directed to nanoparticles, particularly to pyrene functionalized silica nanoparticles for detection of mercury ions in an aqueous solution.

Description of Related Art

The "background" description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present invention.

Mercury ($Hg^0$, $Hg^+$, $Hg^{2+}$) contamination in the environment has increased 3 to 6 fold in recent decades compared to pre-industrial estimates. This poses serious threats to human health, as mercury poisoning causes brain and neurological damage, birth deformities, kidney damage, digestive system problems, memory loss, and language impairments.

Conventionally, various analytical techniques are engaged to monitor $Hg^{2+}$ concentration, such as atomic absorption spectroscopy (AAS), inductively coupled plasma-mass spectrometry (ICP-MS), and plasma-atomic emission spectrometry (AES), gas chromatography (GC), and reversed-phase high-performance liquid chromatography (HPLC). However, these techniques require expensive, specialized, and cumbersome sample preparations and bulky laboratory equipment that make it challenging to adapt for remote sensing applications. Optical methods based on fluorescence sensing have gained much attention, because fluorescence-based chemical sensors offer rapid analysis, better sensitivity, low limit of detection, and high selectivity for investigation of environmental pollutants even at low concentrations. Therefore, there exists a need to develop a cost-effective, sensitive, selective, and convenient portable sensor that can detect $Hg^{2+}$ ions.

SUMMARY

In an exemplary embodiment, a method of detecting mercury ($Hg^{2+}$) ions in an aqueous solution is described. The method includes contacting the aqueous solution with a chemosensor to form a mixture, and further monitoring a change in a fluorescence emission profile of the chemosensor in the mixture to determine a presence or absence of $Hg^{2+}$ ions in the aqueous solution. The chemosensor includes pyrene silica nanoparticles where at least one pyrene is bonded to a surface of a silica nanoparticle through an amide bond with a formula of, pyrene-C(=O)NHR-silica nanoparticle and where R is an alkyl chain.

In another embodiment, R is —$CH_2CH_2CH_2$—.

In another embodiment, the pyrene silica nanoparticles have a uniform size distribution; and an average size of 30-50 nanometers (nm).

In another embodiment, the pyrene silica nanoparticles have a substantially spherical shape.

In another embodiment, the pyrene silica nanoparticles have an amorphous structure.

In another embodiment, the pyrene silica nanoparticles have a positively charged surface; and a zeta potential of 35-45 millivolts (mV).

In another embodiment, the pyrene silica nanoparticles are agglomerated to form a mesoporous structure. In another embodiment, the elements silica (Si), oxygen (O), carbon (C), and nitrogen (N) are homogeneously distributed throughout the mesoporous structure.

In another embodiment, the pyrene silica nanoparticles have a Brunauer-Emmett-Teller (BET) surface area of 30-60 square meters per gram ($m^2/g$).

In another embodiment, the pyrene silica nanoparticles have a total pore volume of 0.25-0.4 grams per cubic centimeter ($cm^3/g$).

In another embodiment, the pyrene silica nanoparticles have an average pore size of 20-30 nm.

In another embodiment, the pyrene silica nanoparticles are stable up to 200 degrees centigrade (° C.).

In another embodiment, the method includes monitoring the change in the fluorescence emission profile of the chemosensor between 350-550 nm.

In another embodiment, the change in the fluorescence emission profile is measured by the disappearance of a fluorescence band from 360 to 425 nm.

In another embodiment, the change in the fluorescence emission profile is measured by the appearance of a fluorescence band from 400 to 525 nm.

In another embodiment, the change in the fluorescence emission profile linearly correlates with the concentration of $Hg^{2+}$ in the aqueous solution.

In another embodiment, the method further includes quantifying the change in the fluorescence emission profile to determine a concentration of $Hg^{2+}$ ions in the aqueous solution.

In another embodiment, the chemosensor is selective for detecting $Hg^{2+}$ ions.

In another embodiment, the aqueous solution further comprises at least one metal cation selected from the group consisting of sodium ($Na^+$), potassium ($K^+$), calcium ($Ca^{2+}$), magnesium ($Mg^{2+}$), barium ($Ba^{2+}$), and silver ($Ag^+$) ions, and the change in the fluorescence emission profile occurs only in the presence of $Hg^{2+}$.

In another embodiment, the limit of detection (LOD) for $Hg^{2+}$ ions is 10 parts per billion (ppb).

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
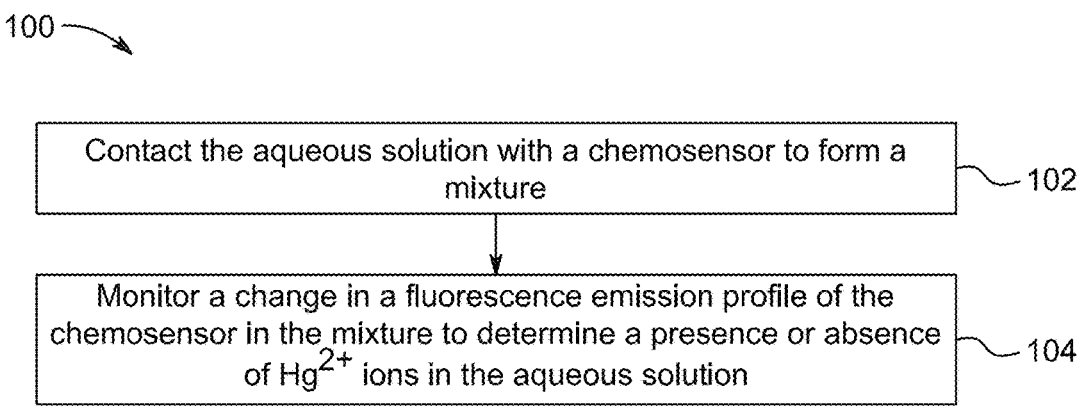
FIG. 1 is a schematic flow diagram of a method of detecting mercury ($Hg^{2+}$) ions in an aqueous solution, according to certain embodiments.

In the drawings, reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

As used herein, the term, "aqueous solution" refers to a solution in which the solvent is mainly water or only water.

As used herein, the term "chemosensor" refers to a molecular structure (organic or inorganic complexes) used to sense an analyte to produce a detectable change or signal.

As used herein, the term "fluorescence" refers to a process where a material absorbs light at high energy, short wavelength, and emits light at lower energy, usually visible, wavelength.

As used herein, the term "emission" refers to a process of elements releasing different photons of color as their atoms return to their lower energy levels.

As used herein, the term "nanoparticles" refers to a small particle that ranges between 1 to 1,000 nanometers in size.

As used herein, the term "amorphous" refers to a shapeless or without definite character or nature.

As used herein, the term "amide bond" refers to RC(=O)NR'R", wherein R, R', and R" represent organic groups or hydrogen atoms.

Embodiments of the present disclosure are directed a method of detecting mercury (Hg$^{2+}$) ions in an aqueous solution using pyrene functionalized silica nanoparticles (Pyr-NH@SiO$_2$ NPs). The synthesized NH$_2$@SiO$_2$NPs and Pyr-NH@SiO$_2$ NPs were thoroughly investigated by proton nuclear magnetic resonance ($^1$H-NMR), Fourier-transform infrared (FTIR), X-ray powder diffraction (XRD), field emission scanning electron microscopy (FESEM), energy-dispersive X-ray spectroscopy (EDS), thermogravimetric analysis (TGA), Brunauer-Emmett-Teller (BET) surface area, and dynamic light scattering (DLS) techniques. The Pyr-NH@SiO$_2$ NPs were used as a chemosensor for Hg$^{2+}$ ions and the presence of Hg$^{2+}$ ions is measured with photoluminescence (PL) spectroscopy. The results indicate that the chemosensor can selectively detect Hg$^{2+}$ ions in the presence of ubiquitous ions (sodium (Na$^+$), potassium (K$^+$), calcium (Ca$^{2+}$), magnesium (Mg$^{2+}$), barium (Ba$^{2+}$), silver (Ag$^+$) and in seawater samples. The change in fluorescence properties with Hg$^{2+}$ ions with a limit of detection (LOD) of 10 parts per billion (ppb) indicates that the Pyr-NH@SiO$_2$ NPs may be effectively utilized as a promising chemosensor for mercury ion detection in aqueous environments.

In an embodiment, the chemosensor includes Pyr-NH@SiO$_2$ NPs. In another embodiment, at least one pyrene is bonded to a surface of a silica nanoparticle through an amide bond. In an embodiment, the amide bond is at any position (1-10) on the pyrene of formula I. In an embodiment, the amide bond is at the 2 or 7 position. In an embodiment, the pyrene may be functionalized on at least one position (1-10) other than the amide bond with a group such as but not limited to an alkyl, a halide, an amine, a carbonyl, an ester, a nitrile, an alcohol, and a carboxylic acid. In an embodiment, the pyrene is functionalized with another pyrene at a position other than the amide bond.

(I)

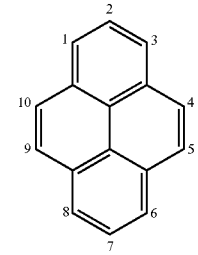

In an embodiment, the Pyr-NH@SiO$_2$ NPs have a formula of pyrene-C(=O)—NHR-silica nanoparticle, and R is an alkyl chain. In an embodiment, R is an alkyl chain comprising 1-20 carbons, preferably 2-19, 3-18, 4-17, 5-16, 6-15, 7-14, 8-13, 9-12, 10-11 carbons. In an embodiment, the alkyl chain can be saturated or unsaturated. In another embodiment, R is a 3 carbon chain, —CH$_2$CH$_2$CH$_2$—.

In an embodiment, the FTIR spectrum of the pyrene silica nanoparticles (FIG. 4B) exhibits an aromatic ring stretch at 3000-3100 cm$^{-1}$, preferably 3010-3080 cm$^{-1}$, 3030-3050 cm$^{-1}$, and carbonyl group (C=O) stretching bands at 1700-1750 cm$^{-1}$, preferably 1710-1740 cm$^{-1}$, 1720-1730 cm$^{-1}$, indicating the presence of pyrene bonded to the silica nanoparticle surface. In an embodiment, at least 20%, preferably 30%, 40%, 50%, 60%, 70%, 80%, 90% or 100% of the surface of the silica nanoparticles is bonded to a pyrene. In some embodiments, the pyrene silica nanoparticles have a uniform size distribution. In some embodiments, the pyrene silica nanoparticles have a size distribution greater than 10 nm, preferably 15 nm, 20 nm, 30 nm or 50 nm. In some embodiments, the pyrene silica nanoparticles have an average size of 30-50 nm, preferably 35-45 nm, or approximately 40 nm. In some embodiments, the pyrene silica nanoparticles have a substantially spherical shape. In some embodiments, the pyrene silica nanoparticles have an irregular shape. In another embodiment, the pyrene silica nanoparticles have an amorphous structure. In some embodiments, the pyrene silica nanoparticles exhibit an XRD peak at 15-30°, preferably 18-27°, or 21-24° (FIG. 5). In some embodiments, no other XRD peaks were detected indicating high purity. In some embodiment, there is less than 1 wt. % impurity in the pyrene silica nanoparticles such as but not limited to trace metals, and unreacted pyrene.

In another embodiment, the pyrene silica nanoparticles are agglomerated to form a mesoporous structure. In some embodiments, the elements silica (Si), oxygen (O), carbon (C), and nitrogen (N) are homogeneously distributed throughout the mesoporous structure. In some embodiments, the agglomerates are greater than 200 nm in size, preferably 200-2,000 nm, 500-1,500 nm, or approximately 1,000 nm. In another embodiment, the pyrene silica nanoparticles are agglomerated through π-π interactions of the pyrenes on the surface. In another embodiment, the pyrene silica nanoparticles are agglomerated through van der waals interactions, C—H . . . π interactions, and dipole-dipole interactions. In some embodiments, the pyrene silica nanoparticles have a positively charged surface, and a zeta potential of 35-45 mV, preferably 38-42 mV, or approximately 40 mV. The high zeta potential value indicates that the pyrene silica nanoparticles are stable in water due to the formation of stable hydrogen bonding with water molecules in the presence of N—H and C=O groups.

In some embodiments, the pyrene silica nanoparticles have a BET surface area of 30-60 m$^2$/g, preferably 35-55 m$^2$/g, 40-50 m$^2$/g, or approximately 45 m$^2$/g. In some embodiments, the pyrene silica nanoparticles have a total pore volume of 0.25-0.4 cm$^3$/g, preferably 0.28-0.38 cm$^3$/g, 0.3-0.35 cm$^3$/g, or 0.32-0.34 cm$^3$/g. In some embodiments, the pyrene silica nanoparticles have an average pore size of 20-30 nm, preferably 22-28 nm, or 24-26 nm. In some embodiments, the BET surface area, total pore volume, and average pore size are less than a silica nanoparticle without a pyrene, because the pyrenes block the pore surfaces and walls. In some embodiments, the pyrene silica nanoparticles are stable up to 200° C., preferably 150-200° C., 160-190° C., or 170-180° C.

Referring to FIG. 1, a schematic flow diagram of the method 100 of detecting Hg$^{2+}$ ions in an aqueous solution is illustrated. The order in which the method 100 is described is not intended to be construed as a limitation, and any number of the described method steps may be combined in any order to implement the method 100. Additionally, individual steps may be removed or skipped from the method 100 without departing from the spirit and scope of the present disclosure.

At step 102, the method 100 includes contacting the aqueous solution with the chemosensor to form a mixture. In an embodiment, the aqueous solution is any water based solution including but not limited to seawater, brackish water, and tap water. In an embodiment, the chemosensor is contacted with the aqueous solution at a temperature range of 15-45° C., preferably 20-40° C., 25-35° C., or approximately 30° C. In an embodiment, the contacting occurs by pouring a solution of the chemosensor into the aqueous solution. In an embodiment, the contacting occurs by adding a powder form of the chemosensor into the aqueous solution. In an embodiment, the chemosensor is mixed into the aqueous solution by a method such as but not limited to, manually stirring, using a stir bar, or a probe sonicator. In an embodiment, the chemosensor is 20 ppm in the aqueous solution, preferably 10 ppm, 5 ppm or 1 ppm.

At step 104, the method 100 includes monitoring a change in a fluorescence emission profile of the chemosensor in the mixture to determine the presence or absence of Hg$^{2+}$ ions in the aqueous solution. In an embodiment, the fluorescence is measured with a spectrofluorometer. In an embodiment, the chemosensor is excited with light with a wavelength of 300-380 nm, preferably 310-370 nm, 320-360 nm, 330-350 nm, or approximately 340 nm and a bandwidth of 1-20 nm, preferably 5-15 nm, or approximately 10 nm. In some embodiments, the change in the fluorescence emission profile of the chemosensor is monitored between 350-550 nm, preferably 375-525 nm, 400-500 nm, 425-475 nm or approximately 450 nm. In some embodiments, the change in the fluorescence emission profile is measured by the disappearance of a fluorescence band from 360 to 425 nm, preferably 370-410 nm, 380-400 nm, or approximately 390 nm. In another embodiment, the change in the fluorescence emission profile is measured by the appearance of a fluorescence band from 400 to 525 nm, preferably 420-500 nm, 440-480 nm, or approximately 460 nm. In an embodiment, the decrease in the fluorescence band between 360 to 425 nm and the increase in the fluorescence band between 400 to 525 nm indicates the presence of Hg$^{2+}$ in the aqueous solution. In an embodiment, the change in fluorescence intensities can be attributed to photoinduced electron transfer to the pyrene molecules and the formation of a stable Hg-pyrene complex with the emitting chromophore. In an embodiment, the change in fluorescence is detected by eye following exposure of the aqueous solution with the chemosensor to an excitation light source.

In some embodiments, the change in the fluorescence emission profile linearly correlates with the concentration of Hg$^{2+}$ in the aqueous solution. In other words, the greater the concentration of the Hg$^{2+}$ ions in the aqueous system, the stronger the change in signal. In some embodiments, the change in the fluorescence emission profile is quantified to determine a concentration of Hg$^{2+}$ ions in the aqueous solution.

In another embodiment, the chemosensor is selective for detecting Hg$^{2+}$ ions. In another embodiment, the aqueous solution further comprises at least one metal cation selected from the group consisting of Na$^+$, K$^+$, Ca$^{2+}$, Mg$^{2+}$, Ba$^{2+}$, and Ag$^+$. In an embodiment, the metal ions in the aqueous solution may be Li$^+$, Na$^+$, K$^+$, Be$^{2+}$, Mn$^{2+}$, Fe$^{2+}$, Co$^{2+}$, Ni$^{2+}$, Cu$^{2+}$, Zn$^{2+}$, Cd$^{2+}$, Se$^{3+}$, Ti$^{3+}$, V$^{3+}$, Cr$^{3+}$, Fe$^{3+}$, Rh$^{3+}$, Ga$^{3+}$, In$^{3+}$, Ce$^{4+}$, Th$^{4+}$, Pa$^{4+}$, U$^{4+}$, Np$^{4+}$, Pu$^{4+}$, Mg$^{2+}$, Ca$^{2+}$, Sr$^{2+}$, Ba$^{2+}$, Al$^{3+}$, Y$^{3+}$, La$^{3+}$, Ag$^+$, Tl$^+$, Pb$^{2+}$, Ti$^{3+}$, Bi$^{3+}$, Sn$^{2+}$, Sn$^{2+}$, or Pd$^{2+}$. In an embodiment, the change in the fluorescence emission profile occurs only in the presence of Hg$^{2+}$. In some embodiments, the limit of detection for Hg$^{2+}$ ions is 10 ppb, preferably 5 ppb or 1 ppb.

EXAMPLES

The following examples describe and demonstrate exemplary embodiments of a method of detecting mercury (Hg$^{2+}$) ions in an aqueous solution described herein. The examples are provided solely for the purpose of illustration and are not to be construed as limitations of the present disclosure, as many variations thereof are possible without departing from the spirit and scope of the present disclosure.

Example 1: Materials

All the chemicals and reagents, including cetyltrimethylammonium bromide (CTAB, ≥98%, Sigma-Aldrich), sodium hydroxide (AG, Fluka), tetraethyl orthosilicate (TEOS, ≥99%, Sigma-Aldrich), 3-aminopropyl triethyl silane (APTS, 99%, Sigma-Aldrich), 1-pyrene carboxylic acid (97%, Sigma-Aldrich), hydroxy benzotriazole (≥97%, Sigma-Aldrich), 1-ethyl-3-(3-dimethyl aminopropyl)carbodiimide hydrochloride (≥99%, Sigma-Aldrich), triethylamine (≥99%, Sigma-Aldrich), ethyl acetate (High-performance liquid chromatography (HPLC), Honeywell) were purchased and utilized without further purification.

Example 2: Synthesis of Silica Nanoparticles (NH2@SiO$_2$NPs)

The synthesis of silica nanoparticles (NPs) was carried out by Stober's method using silane precursors. For this purpose, 2.0 grams of CTAB surfactant was dissolved in 25 milliliters (mL) of de-ionized water under vigorous stirring and transferred into a round bottom flask containing a solution of sodium hydroxide (NaOH) (0.70 g) and deionized water (100 mL). Then, 25 mL of ethyl acetate was added to the reaction mixture and continued stirring for 10 min (minutes), followed by the addition of tetraethyl orthosilicate (TEOS) (3.20 mL). The reaction contents were stirred for another 40 min at room temperature, followed by the addition of 2.1 mL of 3-aminopropyl) triethoxysilane (APTS), and kept the reaction contents to stir overnight. The mixture was centrifuged at 10,000 revolutions per minute (rpm) to separate the amino-functionalized silica nanoparticles (product). The product was washed thrice with de-ionized water and twice with absolute ethanol to remove the surfactant and impurities. The synthesized silica NPs were further transferred into a petri dish, and the solvent (ethanol) was allowed to evaporate in a vacuum oven at 60 degrees centigrade (° C.) to yield a fine white powder of silica (NH$_2$@SiO$_2$NPs) with an experimental yield of ~80%.
Fourier transform infrared (FTIR) (neat): ν (cm$^{-1}$)=3444, 2922, 2852, 1643, 1553, 1471, 1056, 785, 451.
proton nuclear magnetic resonance ($^1$H-NMR) (400 MHz, DMSO): δ=1.243 (m, 2H), 2.33 (t, 2H), 2.67 (t, 2H).

Example 3: Synthesis of Pyrene-Attached Silica Nanoparticles (Pyr-NH@SiO2 NPs)

The amino-functionalized silica NPs (0.200 g) and 1-pyrene-carboxylic acid (0.300 g) were taken into a dried round bottom flask (50 mL), followed by the addition of hydroxy benzotriazole (0.210 g) and 1-ethyl-3-(3-dimethyl aminopropyl) carbodiimide hydrochloride (0.232 g). Subsequently, anhydrous chloroform (20 mL) was added to the flask and stirred into the reaction mixture. Further, triethylamine (0.356 ml) was added to the reaction mixture, and the stirring was continued at room temperature for 24 hours. After completion of the reaction, the flask contents were transferred into a separatory funnel, and ethyl acetate (40 mL) was added. The product was washed twice with NaOH solution (1 Molar (M), 20 mL) and de-ionized water to remove the unwanted coupling reagents and unreacted pyrene-carboxylic acid. Finally, the organic solvent was removed using a rotary evaporator to get the final product (Pyr-NH@SiO$_2$ NPs) as a yellow powder.
FTIR (neat): ν(cm–1)=3415, 3035, 2926, 2853, 1740, 1642, 1569, 1448, 1383, 1261, 1092, 844, 741, 451.
$^1$H-NMR (400 MHz, DMSO): δ=1.463 (m, 2H), 2.985 (t, 2H), 4.515 (t, 2H), 8.160-859 (m, 7H), 8.613 (dd, 1H), 9.109 (dd, 1H).

Example 5: Characterization Techniques $^1$H-NMR spectra were recorded on a 400-megahertz (MHz) spectrometer (Bruker AVANCE III) using 3-(trimethylsilyl)-1,3-oxazolidin-2-one (TMSO) as an internal standard and dimethyl sulfoxide (DMSO) as a deuterated solvent. Fourier transformed infrared (FTIR) spectra were attained on a spectrophotometer (Perkin Elmer 16F PC, Perkin Elmer Inc. USA). The phase of silica NPs was evaluated by X-ray diffractometer (Rigaku MiniFlexII, Japan) with Cu Kα1 radiation (γ=0.15416 nanometers (nm)). Surface morphology and particle size of silica samples were investigated via field emission scanning electron microscope (FESEM) (Lyra-3, Tescan, Czech Republic), having an accelerating voltage up to 30 kilovolts (kV). A dilute dispersion of each sample was dried on a stub having Cu-tape followed by Au-coating. Energy dispersive X-ray (EDX) silicon-drift detector (X-Max☐N, Oxford Instruments, UK) coupled with a FESEM were engaged to determine the presence and ratio of elemental particles. Thermogravimetric analyses (TGA) were performed on TGA 1 STARe System (Mettler Toledo, US) under Ar atmosphere (flow rate 15 mL min$^{-1}$) from 20 to 800° C. at a rate of 10° C. min$^{-1}$. A Brunauer-Emmett-Teller (BET) surface area of materials was estimated by N$_2$ adsorption-desorption using a Micromeritics (ASAP 2010) analyzer. The surface charge and zeta potential values of synthesized NH$_2$@SiO$_2$ NPs and Pyr-NH@SiO$_2$ NPs were evaluated using Zetasizer nano (ZEN3600, Malvern, UK). The silica samples were dispersed in de-ionized water using a probe sonicator (UPT-400, Hielscher) to achieve maximum dispersion of particles before imaging and zeta potential measurements.

Example 6: Photoluminescence Technique for Pyr-NH@SiO$_2$ NPs

To assess the practicality of the nanosensor (Pyr-NH@SiO$_2$ NPs) for mercury ions detection, the sensing material was well-dispersed in de-ionized water using the probe sonicator. A photoluminescence (PL) spectrum of the Pyr-NH@SiO$_2$ NPs was recorded using a spectrofluorometer (FP-8500, JASCO) at an excitation wavelength of 340 nm by adjusting the bandwidth to 5 nm. All the measurements were performed at ambient conditions. The sensing properties of Pyr-NH@SiO$_2$ NPs (20 parts per million (ppm)) were recorded by the successive increase in $Hg^{2+}$ ions concentration within the range from 0-50 ppm. Finally, the selectivity of Pyr-NH@$SiO_2$ NPs against $Hg^{2+}$ ions was examined in the presence of ubiquitous ions (sodium ($Na^+$), potassium ($K^+$), calcium ($Ca^{2+}$), magnesium ($Mg^{2+}$), barium ($Ba^{2+}$), and silver ($Ag^+$), and seawater (SW) samples. The total salinity of the seawater sample was 36.03 g $L^{-1}$.

Example 7: Synthesis Chemistry of Pyr-NH@$SiO_2$ NPs

Figure 2:
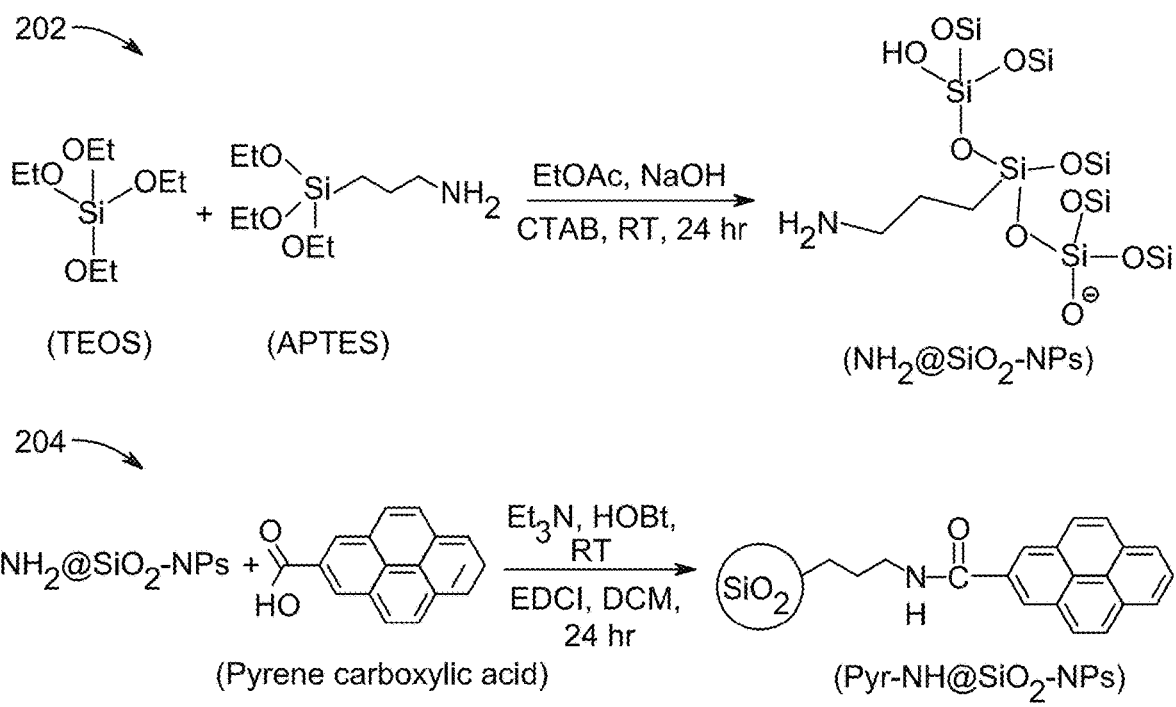
FIG. 2 illustrates a schematic procedure of pyrene attached silica nanoparticles (Pyr-NH@$SiO_2$ NPs) synthesis, according to certain embodiments.

Stober's method was considered the most efficient and straightforward in terms of reaction conditions and high experimental yield. FIG. 2 illustrates Stober's method for preparing mono-dispersed spherical silica nanoparticles. At step 202, the method includes hydrolysis of TEOS followed by a condensation reaction using ethyl acetate in the presence of sodium hydroxide and CTAB surfactant. The surface of silica NPs was amino-functionalized to achieve $NH_2$@$SiO_2$ NPs by utilizing APTS under the same reaction conditions (202). At step 204, the $NH_2$@$SiO_2$ NPs were subjected to amidation with 1-pyrene-carboxylic acid by adding hydroxy benzotriazole and 1-ethyl-3-(3-dimethyl aminopropyl) carbodiimide hydrochloride as peptide coupling agents (FIG. 2). This coupling reaction was also performed by another route where 1-pyrene-carboxylic acid was first converted into an acid chloride using thionyl chloride. The excessive thionyl chloride was removed under reduced pressure or bubbling nitrogen gas in a fume-hood. The acid chloride was further allowed to react directly with $NH_2$@$SiO_2$ NPs in anhydrous chloroform. The final product (Pyr-NH@$SiO_2$ NPs) was extracted with ethyl acetate and washed the organic layer with a saturated solution of sodium bicarbonate to remove excessive or unreacted 1-pyrene carboxylic acid.

Example 8: Structural and Morphological Analyses

Figure 3A:
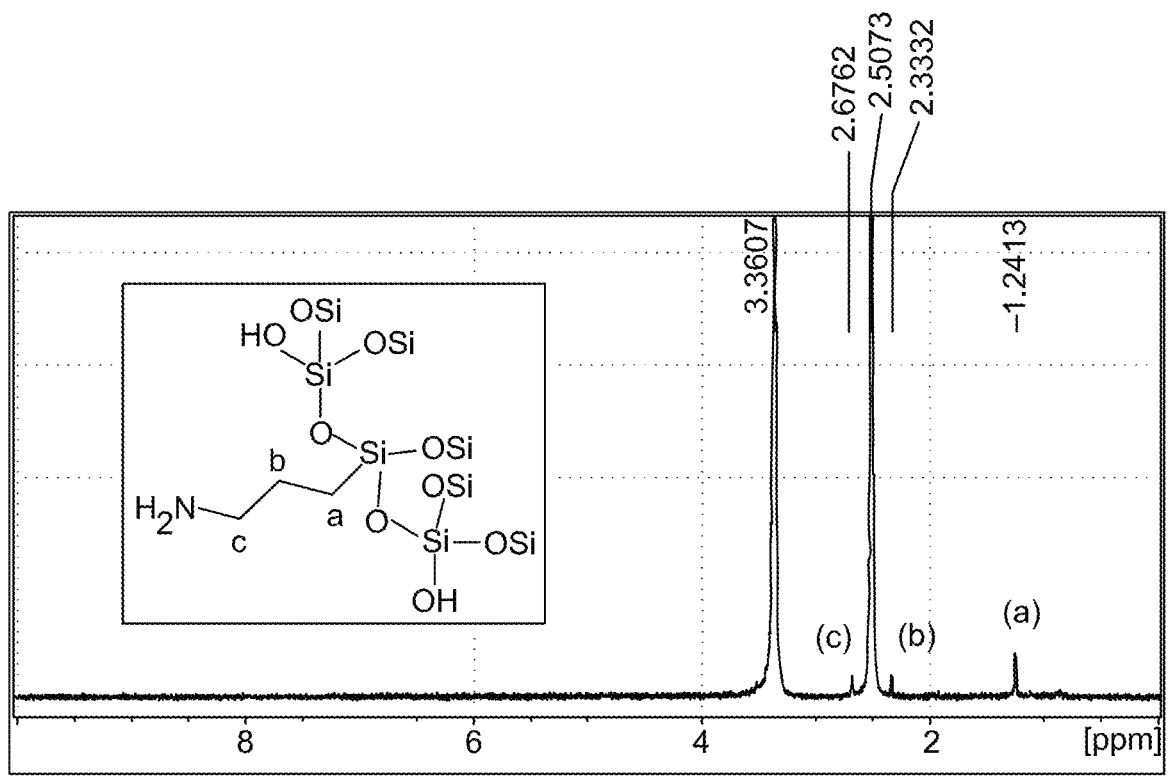
FIG. 3A illustrates a proton nuclear magnetic resonance ($^1$H-NMR) spectra of $NH_2$@$SiO_2$ NPs, according to certain embodiments.
Figure 3B:
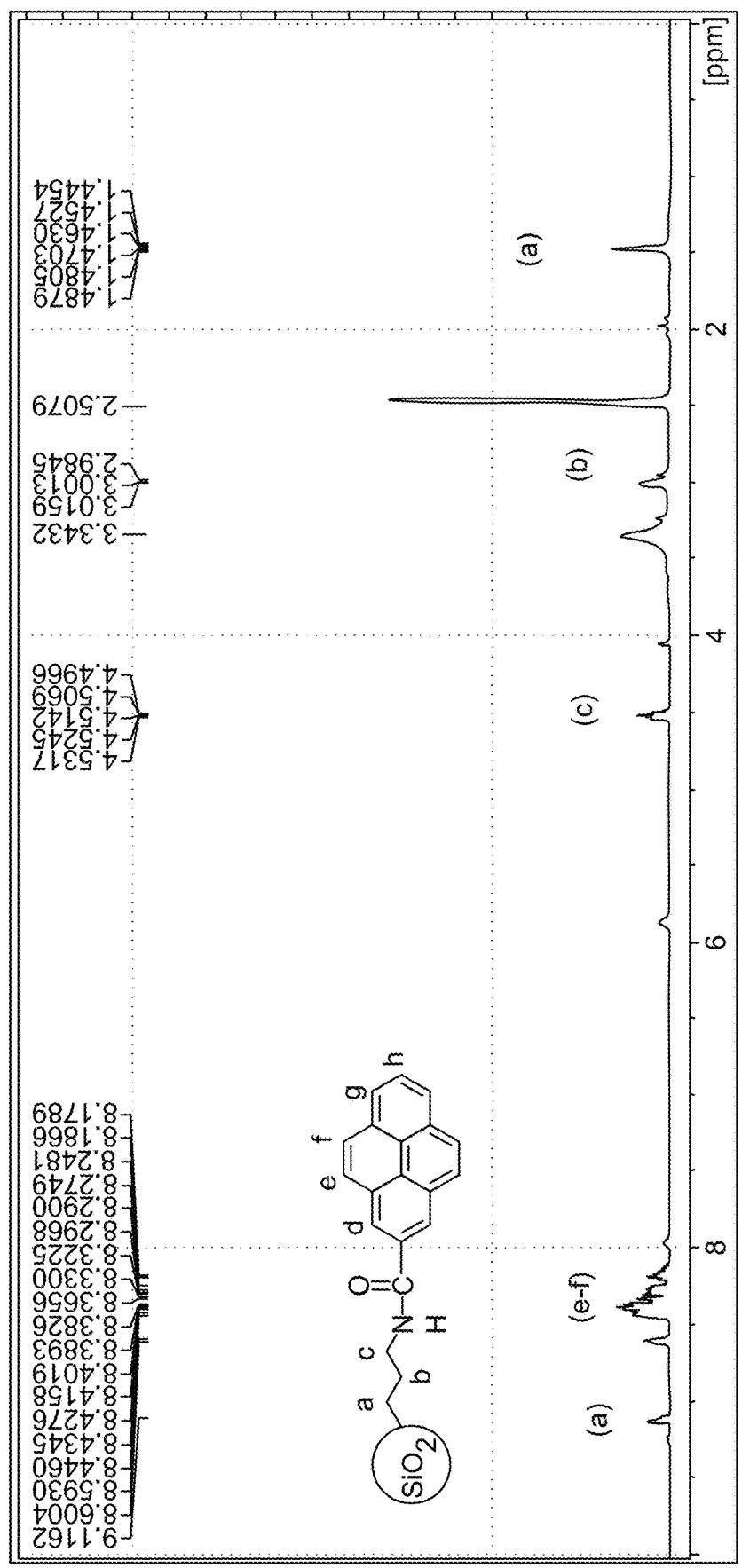
FIG. 3B illustrates $^1$H-NMR spectra of Pyr-NH@$SiO_2$ NPs, according to certain embodiments.

The chemical structures of $NH_2$@$SiO_2$ NPs and Pyr-NH@$SiO_2$ NPs were investigated by $^1$H-NMR, as illustrated in FIGS. 3A and 3B, respectively. The amino-functionalized silica nanoparticles ($NH_2$@$SiO_2$ NPs) have three different methylene (—$CH_2$—) protons. FIG. 3A illustrates the characteristic peak of central methylene protons in the propyl chain (—$CH_2$—$CH_2$—$CH_2$—) appeared at $\delta$=1.24 ppm, methylene protons adjacent to Si—O (—$CH_2$—Si—O) emerged at $\delta$=2.33 ppm, while the methylene protons near terminal amine (—$NH_2$—$CH_2$—) were found at $\delta$=2.67 ppm. Similarly, the chemical structure of the final product (Pyr-NH@$SiO_2$ NPs) was ascertained from $^1$H-NMR (FIG. 3B), where the methylene protons of the amino-propyl component showed significant downfield shifts. The methylene protons that existed adjacent to the amide bond (Pyr-NH—$CH_2$—) appeared at $\delta$=4.51 ppm as compared to $\delta$=2.67 ppm, $CH_2$ near Si—O (—$CH_2$—Si—O) shifted to $\delta$=2.98 ppm, while central $CH_2$ group in propyl chain (—$CH_2$—$CH_2$—$CH_2$—) moved slightly to $\delta$=1.47 ppm from $\delta$=1.24 ppm. FIG. 3B illustrates the aromatic protons of the pyrene ring were found between $\delta$=8.16 ppm to $\delta$=9.11 ppm.

Figure 4A:
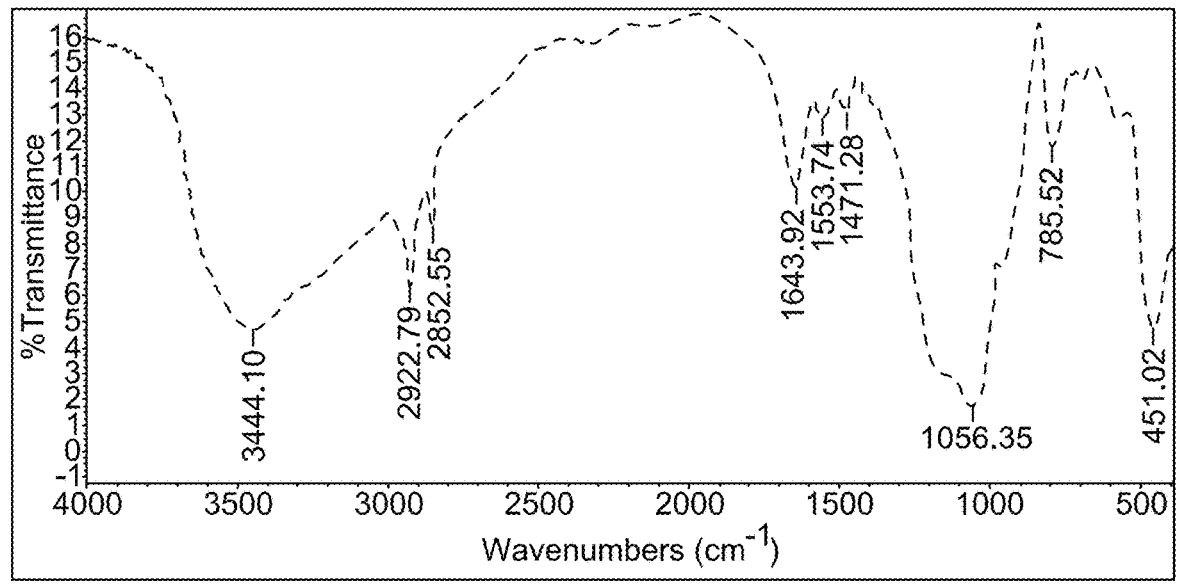
FIG. 4A illustrates a Fourier-transform infrared (FTIR) spectra of the NH$_2$@SiO$_2$ NPs, according to certain embodiments.
Figure 4B:
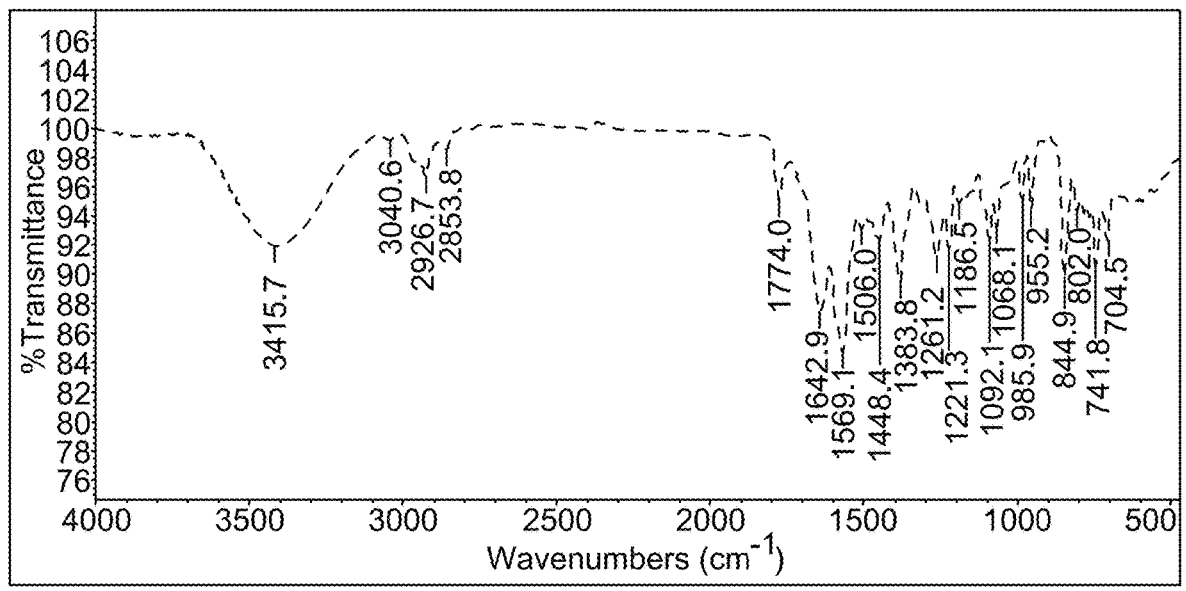
FIG. 4B illustrates FTIR spectra of the Pyr-NH@SiO$_2$ NPs, according to certain embodiments.
Figure 5:
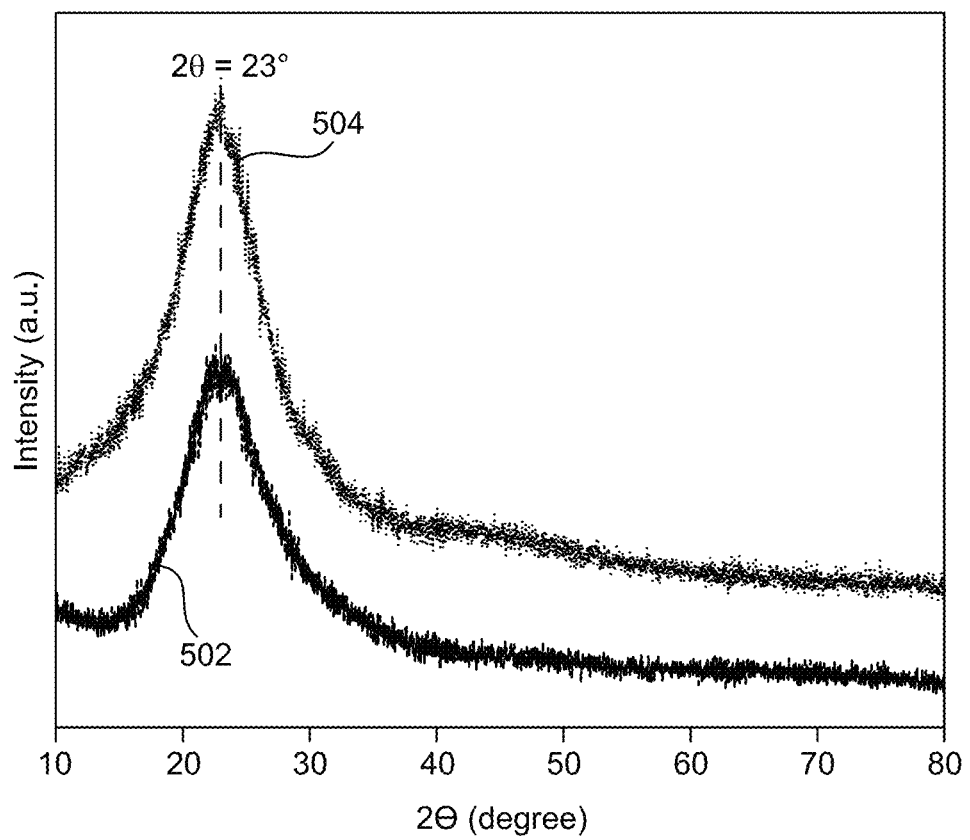
FIG. 5 illustrates an X-ray powder diffraction (XRD) pattern for the NH$_2$@SiO$_2$ NPs and the Pyr-NH@SiO$_2$ NPs, according to certain embodiments.
Figure 6B:
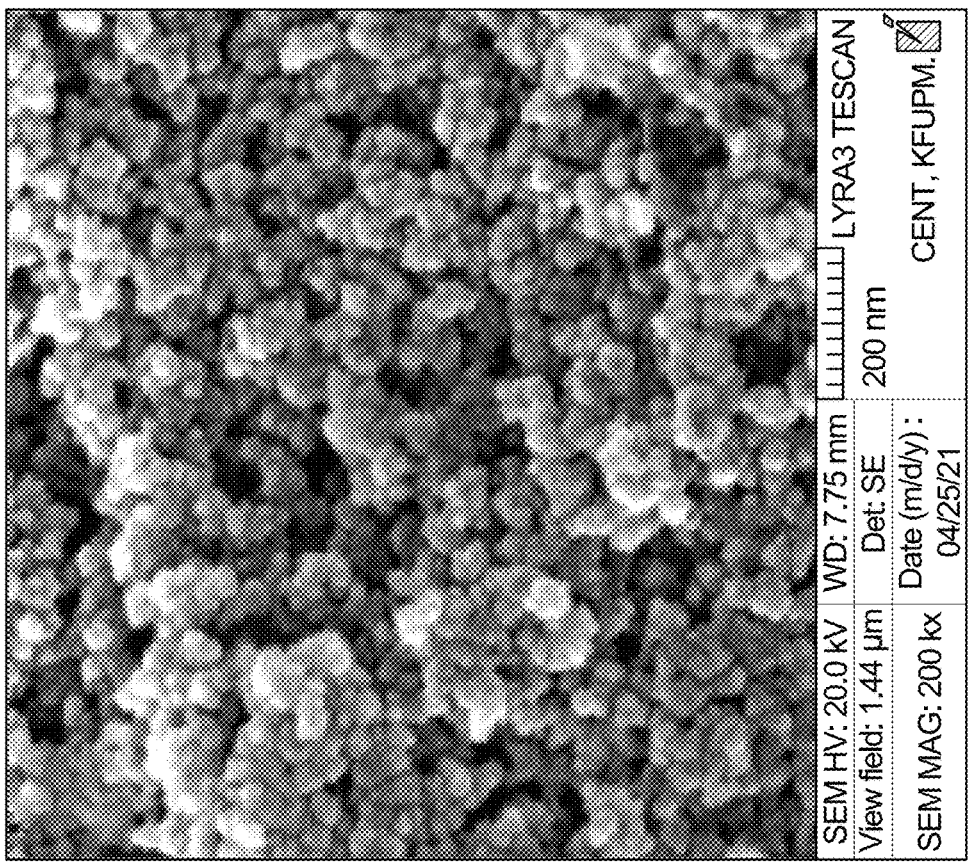
FIG. 6A-6B illustrate a low- and high-resolution field emission scanning electron microscopy (FESEM) images of the NH$_2$@SiO$_2$ NPs, according to certain embodiments.
Figure 6A:
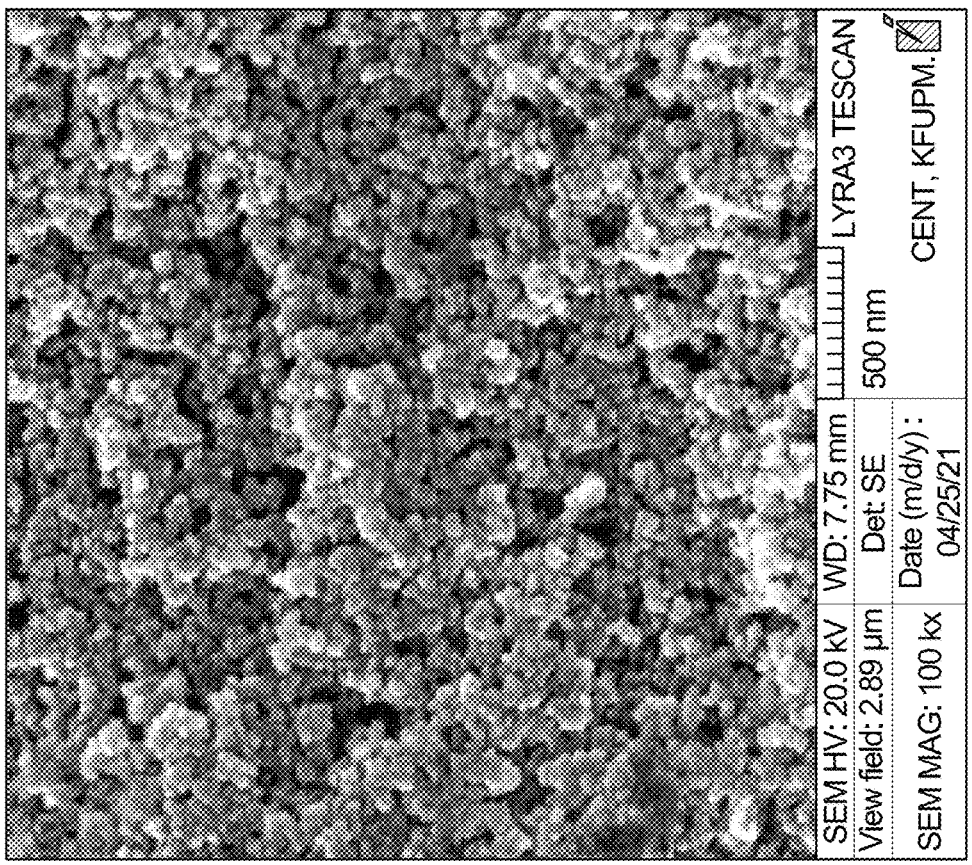
Figure 6D:
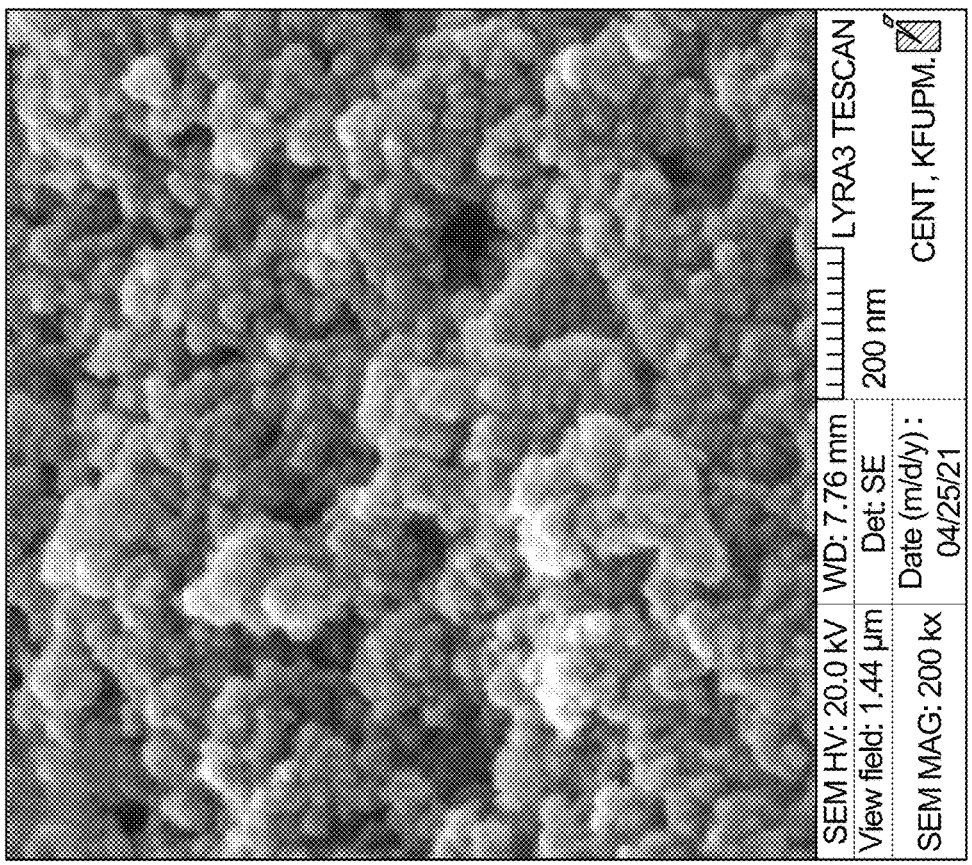
FIG. 6C-6D illustrate a low- and high-resolution FESEM images of the Pyr-NH@SiO$_2$ NPs, according to certain embodiments.
Figure 6C:
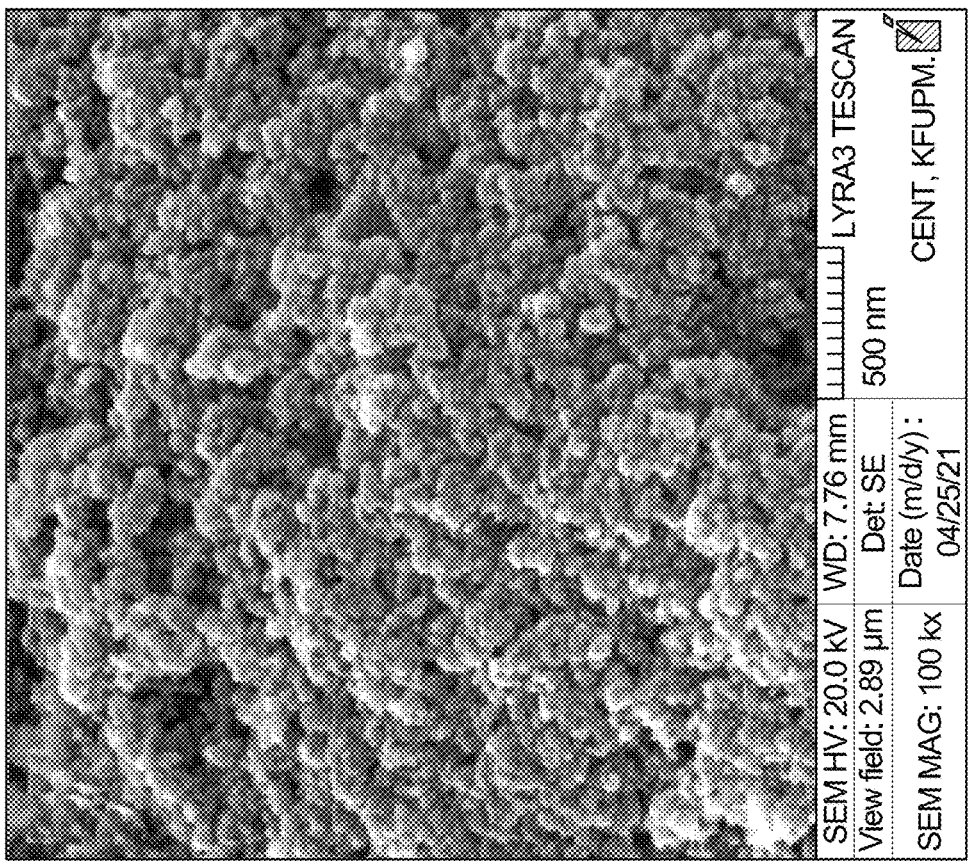
Figure 7A:
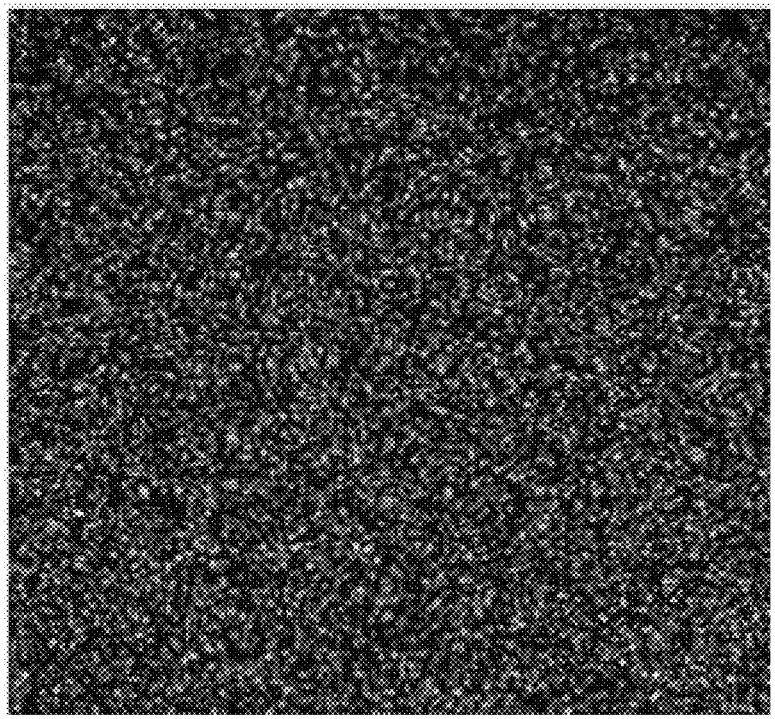
FIG. 7A illustrates an elemental map of the Pyr-NH@SiO$_2$ NPs exhibiting the presence of silica (Si) atom, according to certain embodiments.
Figure 7B:
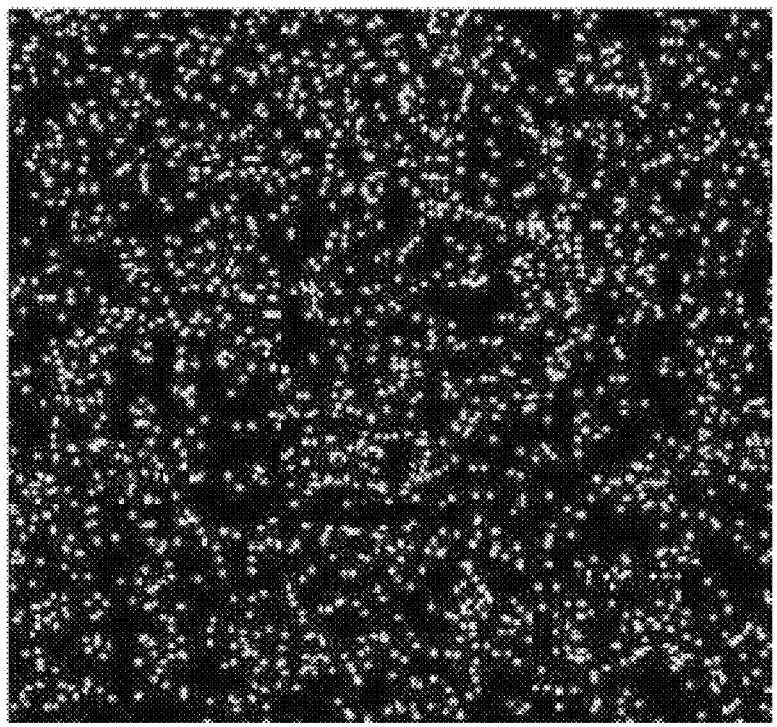
FIG. 7B illustrates an elemental map of the Pyr-NH@SiO$_2$ NPs exhibiting the presence of oxygen (O) atom, according to certain embodiments.
Figure 7C:
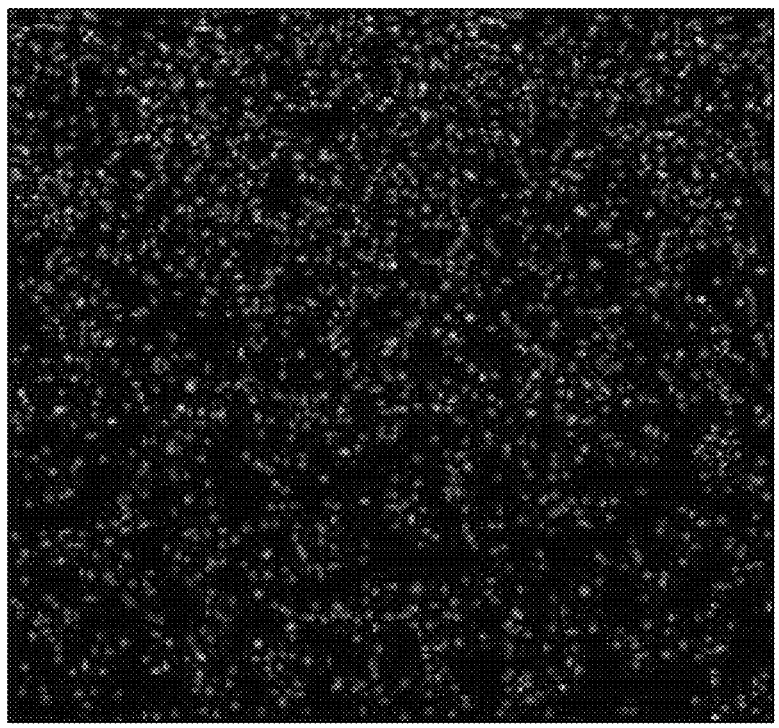
FIG. 7C illustrates an elemental map of Pyr-NH@SiO$_2$ NPs exhibiting the presence of carbon (C) atom, according to certain embodiments.
Figure 7D:
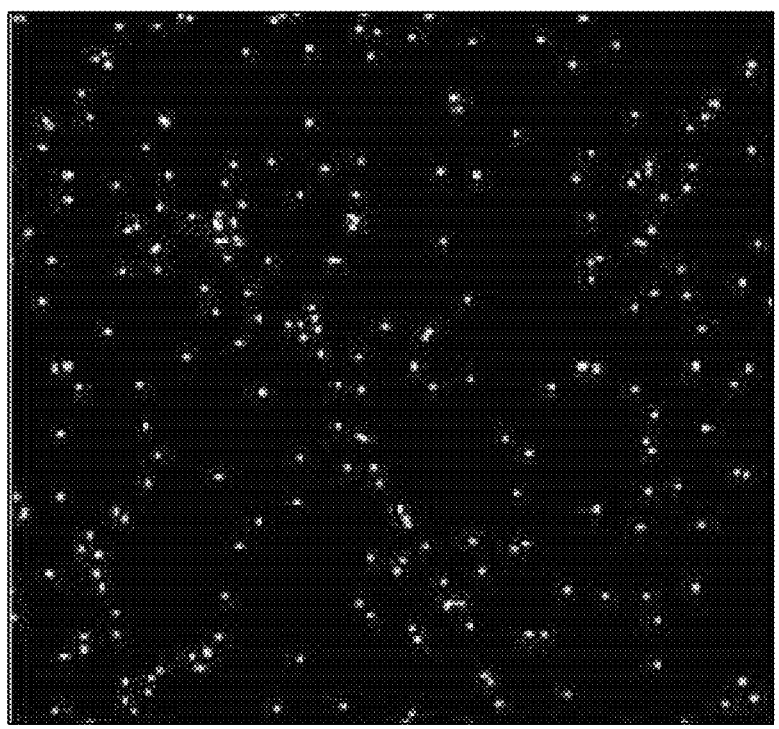
FIG. 7D illustrates an elemental map of the Pyr-NH@SiO$_2$ NPs exhibiting the presence of nitrogen (N) atom, according to certain embodiments.

FIGS. 4A-4B illustrate the functional groups, stretching, and bending vibrations of $NH_2$@$SiO_2$ NPs and Pyr-NH@$SiO_2$ NPs as investigated by FTIR spectroscopy. FTIR spectrum of $NH_2$@$SiO_2$ NPs showed a broad band at 3444 $cm^{-1}$ for N—H stretch that overlapped with hydroxyl (—OH) of silica core or water adsorbed on the surface of the material. However, the broad N—H bending bands could be seen clearly at 1643 $cm^{-1}$. The aliphatic nature of the molecule for the aminopropyl part was fully supported by the stretching bands observed at 2922 $cm^{-1}$ and 2852 $cm^{-1}$, along with bending vibration bands at 1553 $cm^{-1}$ and 1471 $cm^{-1}$. The symmetric and antisymmetric vibration modes of Si—O—Si appeared at 785 $cm^{-1}$ and 1130 $cm^{-1}$, respectively, and its bending vibration was found at 451 $cm^{-1}$. From FIG. 4A, the C—N stretching band was observed at 1056 $cm^{-1}$, strongly overlapped with strong bands of silanol groups and Si—O—Si vibrations. FIG. 4B illustrates the FTIR spectrum of Pyr-NH@$SiO_2$ NPs (final product) showed additional absorption bands for aromatic ring stretch at 3035 $cm^{-1}$ and carbonyl group (C=O) stretching bands at 1740 $cm^{-1}$ along with the characteristic peaks emerged for $NH_2$@$SiO_2$ NPs. The $^1$H-NMR and FT-IR results confirmed the formation of pyrene attached silica nanoparticles.

FIG. 5 illustrates a broad diffraction peak observed at the 2θ position of ~23° (JCDD No., 00-001-0649), confirming the amorphous nature of silica nanoparticles. The crystal structure, phase, and purity of as-synthesized $NH_2$@$SiO_2$ NPs (502) and Pyr-NH@$SiO_2$ NPs (504) were investigated by X-ray diffraction (XRD) analysis. However, no extra peaks were detected, indicating the high purity of synthesized silica NPs. The products were thoroughly washed to remove the surfactant, unwanted coupling reagents, and unreacted pyrene-carboxylic acid. The surface morphology and particle size of as-synthesized silica and pyrene attached silica.

The NPs were examined via field emission scanning electron microscopy (FESEM), and the results of this study are presented in FIG. 6. FIGS. 6A-6D represents low and high-resolution FESEM images of $NH_2$@$SiO_2$ NPs (FIGS. 6A-6B) and Pyr-NH@$SiO_2$ NPs (FIGS. 6C-6D), respectively. The spherical-shaped silica particles are well-dispersed, homogeneous in size, and uniformly distributed over the surface. The average size of $NH_2$@$SiO_2$ NPs and Pyr-NH@$SiO_2$NPs was ~35 and ~40 nm, respectively. The comparison indicates the Pyr-NH@$SiO_2$ NPs were more compact than $NH_2$@$SiO_2$ NPs, which might be due to aggregation occurring by π-π interactions between the organic moieties. Moreover, no significant change in the average size of silica NPs was observed upon attachment with pyrene components. The elemental composition was evaluated via energy-dispersive X-ray spectroscopy (EDS) for the selected micrograph area. FIGS. 7A-7D illustrates the elemental mapping of Pyr-NH@$SiO_2$ NPs, signifying the presence of silica (Si), oxygen (O), carbon (C), and nitrogen (N) atoms, respectively in the investigated sample. The elemental maps exhibit a homogenous distribution of all components.

Figure 8:
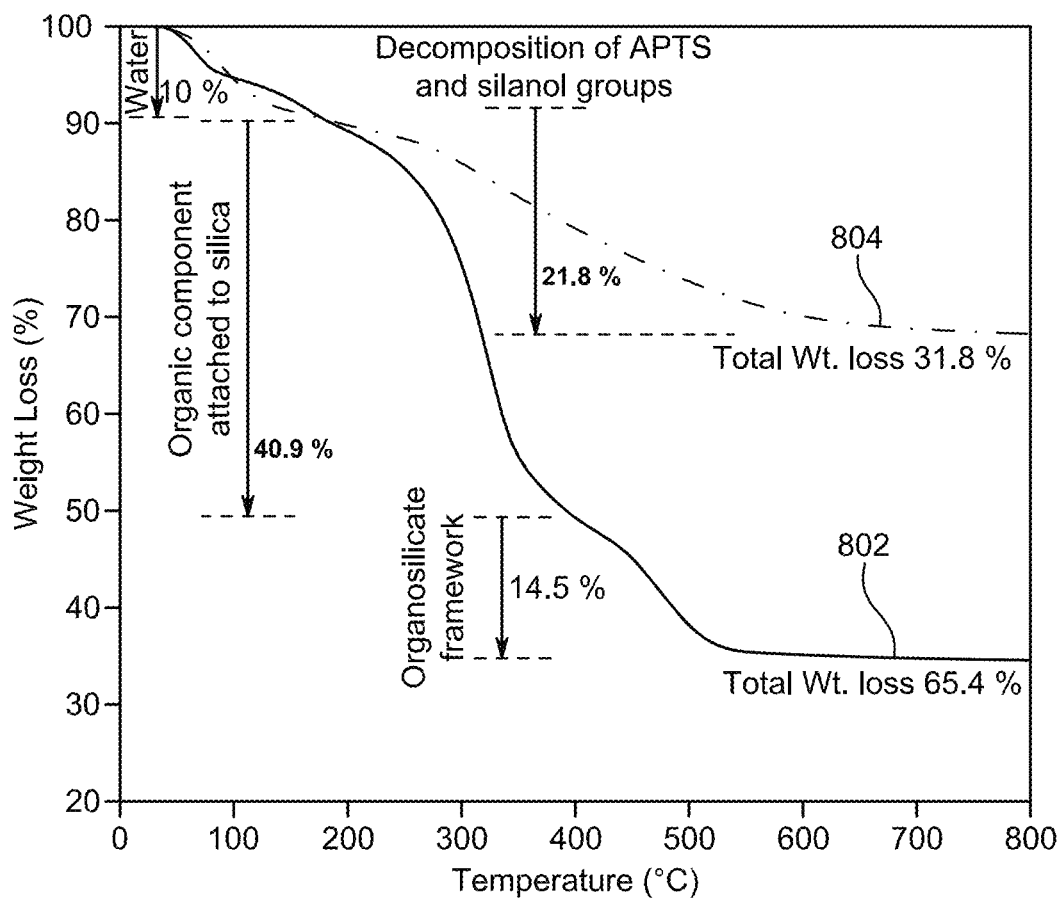
FIG. 8 illustrates thermogravimetric curves (TGA) of the NH$_2$@SiO$_2$ NPs and the Pyr-NH@SiO$_2$ NPs showing a thermal decomposition of organic components and organ silicate frameworks attached to silica nanoparticles, according to certain embodiments.

Further, the thermal stability of the silica materials was performed, and the results of this study are shown in FIG. 8. The thermal stability of pyrene-functionalized silica (Pyr-NH@$SiO_2$ NPs) 802 and amino-functionalized silica ($NH_2$@$SiO_2$ NPs) 804 was investigated from room temperature to 800° C. The first weight loss (~10%) was observed up to 160° C. due to moisture and water molecules that were physically adsorbed on the surface of silica NPs. The weight loss (~21.8%) detected in the region from 160° C. to 800° C. for $NH_2$@$SiO_2$ NPs was mainly due to the thermal decomposition of 3-aminopropyl and silanol groups, confirming the chemical attachment of 3-aminopropyl groups with silica NPs. However, in the case of Pyr-NH@$SiO_2$ NPs, the weight loss was observed in two consecutive steps. In the first step, the weight loss (40.9%) between 160° C. to 400° C. was attributed to the organic components attached to silica, while the weight loss (14.5%) between 400° C. to 600° C. was mainly due to the thermal decomposition of organosilicate frameworks (Si—C, C—N, and C—C bonds). The observed weight losses also confirmed the attachment of pyrene dye with silica NPs. The results indicate that the developed sensor having Pyr-NH@SiO$_2$ NPs was thermally stable enough (up to 200° C.) for practical applications.

Figure 9:
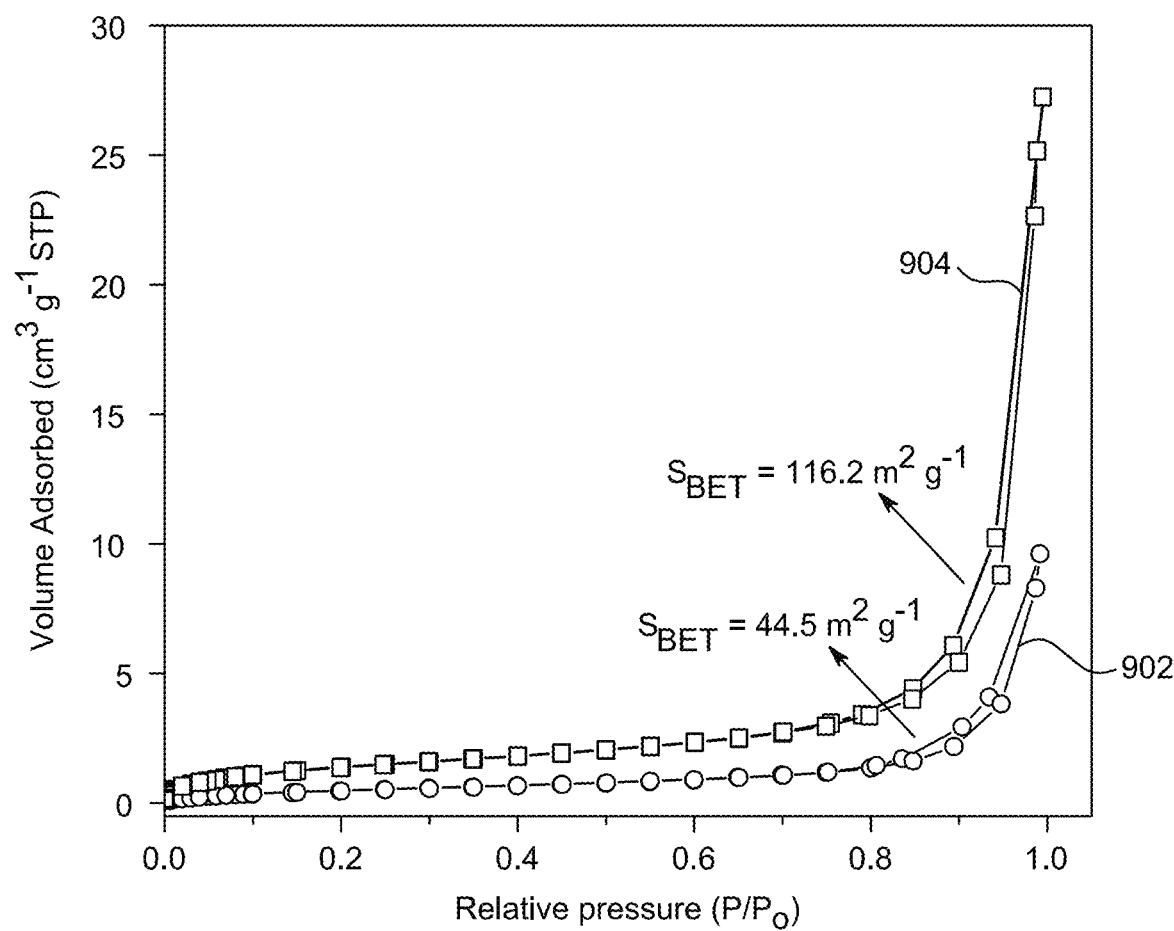
FIG. 9 illustrates nitrogen adsorption-desorption isotherms of the NH$_2$@SiO$_2$ NPs and the Pyr-NH@SiO$_2$ NPs, according to certain embodiments.

FIG. 9 illustrates the curves representing type IV isotherms at high relative pressure suggesting the formation of mesoporous silica materials having uniform size distributions. The surface area and pore structure of NH$_2$@SiO$_2$ NPs 902 and Pyr-NH@SiO$_2$ NPs 904 were assessed by nitrogen adsorption-desorption isotherms obtained parameters such as BET surface area (SBET), total pore volume (V), and average pore diameter (DBJH) were summarized in Table 1.

TABLE 1

| Material | $S_{BET}/(m^2\ g^{-1})$ | $V/(cm^3\ g^{-1})$ | $D_{BJH}/(nm)$ |
|---|---|---|---|
| NH$_2$ @ SiO$_2$ NPs | 116.2 | 0.95 | 30.8 |
| Pyr-NH @ SiO$_2$ NPs | 44.5 | 0.33 | 25.3 |

The comparison indicated that the BET surface area of NH$_2$@SiO$_2$ NPs (116.2 m$^2$ g$^{-1}$) decreased 2.61 times compared to Pyr-NH@SiO$_2$ NPs (44.5 m$^2$ g$^{-1}$). Moreover, the values of Barrett-Joyner-Halenda (BJH) pore sizes reveal that the synthesized NH$_2$@SiO$_2$ NPs (30.8 nm) and Pyr-NH@SiO$_2$NPs (25.3 nm) are mesoporous materials. This decrease in surface area, pore size, and pore volume of Pyr-NH@SiO$_2$ NPs signify the blocking of pore surfaces and channel walls, confirming the presence of fluorescence indicator (pyrene) on the inner surface of silica NPs.

Figure 10A:
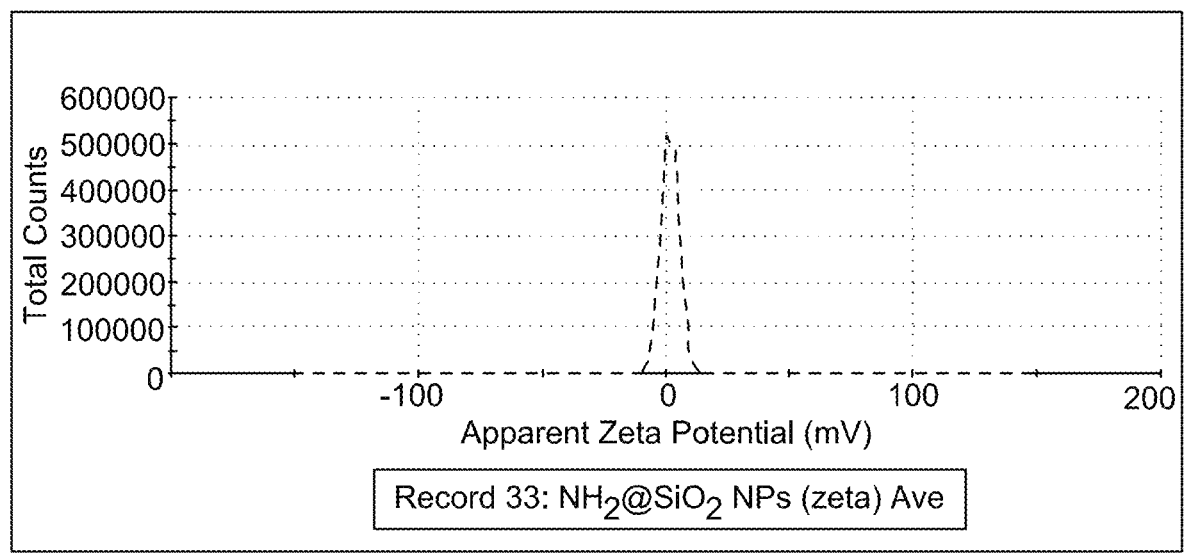
FIG. 10A illustrates a surface charge and zeta potential measurements of the NH$_2$@SiO$_2$ NPs, according to certain embodiments.
Figure 10B:
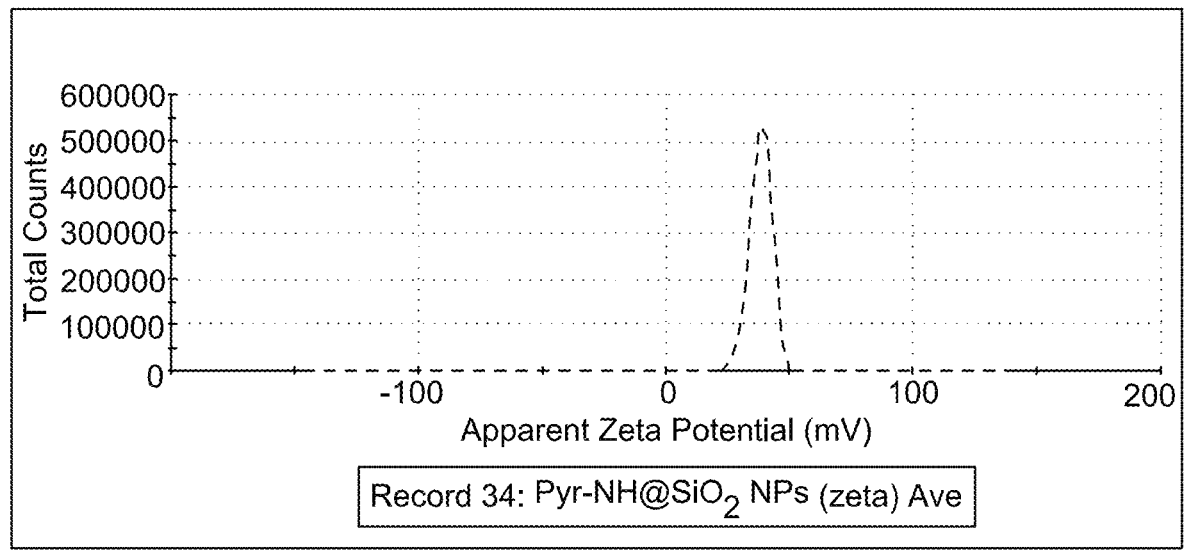
FIG. 10B illustrates a surface charge and zeta potential measurements of the Pyr-NH@SiO$_2$NPs, according to certain embodiments.

The surface charge and zeta potential values of the NPs were estimated in deionized water via the dynamic light scattering (DLS) technique. FIGS. 10A-10B illustrates that NH$_2$@SiO$_2$ NPs and Pyr-NH@SiO$_2$ NPs were positively charged with zeta potential values of 1.69 mV and 38.0 mV, respectively. The comparison indicates that the Pyr-NH@SiO$_2$ NPs were more stable in water after modification with 1-pyrene-carboxylic acid due to the formation of stable hydrogen bonding with water molecules in the presence of N—H and C=O groups. This suggested that Pyr-NH@SiO$_2$ NPs can be successfully deployed as chemosensors in aqueous environments.

Example 9: Fluorescent and Sensing Properties of Pyr-NH@SiO$_2$NPs

The luminescent properties of the powdered and aqueous samples of the NH$_2$@SiO$_2$ NPs and Pyr-NH@SiO$_2$ NPs were examined under normal light and ultraviolet (UV)-light illumination. It was observed that the synthesized Pyr-NH@SiO$_2$ NPs remained dispersed in the aqueous phase and produced bright green fluorescence emission under UV-light illumination. This also indicated the chemical and fluorescence stability of Pyr-NH@SiO$_2$ NPs in the aqueous environment.

Figure 11:
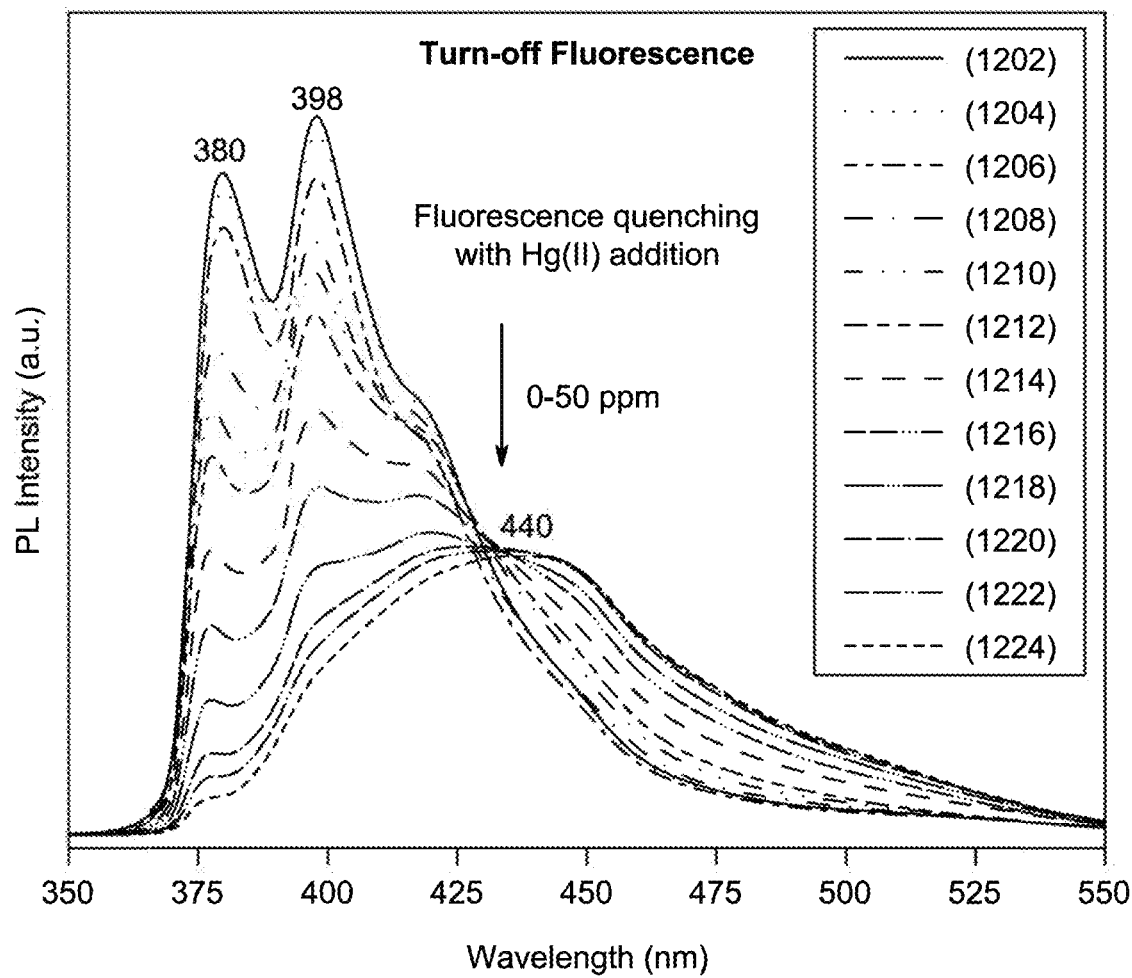
FIG. 11 illustrates a photoluminescence (PL) emission spectrum of the Pyr-NH@SiO$_2$ NPs (20 parts per million (ppm)) before and after exposure to Hg$^{2+}$ ions in a concentration ranging from 0-50 ppm (excitation wavelengths ($\lambda$ex)=340 nm), according to certain embodiments.

The fluorescent properties of Pyr-NH@SiO$_2$ NPs were investigated to check their feasibility for mercury ions detection. FIG. 11 represents photoluminescence (PL) emission spectra of Pyr-NH@SiO$_2$ NPs before and after exposure to Hg$^{2+}$ ions. The changes in fluorescent properties were examined based on peak shift and emission intensity. The PL spectrum of Pyr-NH@SiO$_2$ NPs (20 ppm) exhibited two distinct vibronic bands observed at 380 and 398 nm corresponding to $\pi \rightarrow \pi^*$ transitions in pyrene molecule, which were cumulatively denoted as the monomeric emission. Pyr-NH@SiO$_2$ NPs were further exposed to the known concentrations of Hg$^{2+}$ ions, namely, 0 ppb (1202), 10 ppb (1204), 100 ppb (1206), 250 ppb (1208), 500 ppb (1210), 1.0 ppm (1212), 2.5 ppm (1214), 5.0 ppm (1216), 10 ppm (1218), 10 ppm (1220), 20 ppm (1222), 30 ppm (1224), and 50 ppm (1226). The fluorescence emission intensity of pyrene gradually decreased when Hg$^{2+}$ concentration increased from 0-50 ppm. This gradual decline in fluorescence intensity might be attributed to the possible complexation of Hg$^{2+}$ ions with fluorescent pyrene molecules to form a stable mercury-pyrene complex, which triggers the turn-off (quenching) mechanism. Moreover, it was observed that there was a hypsochromic shift (blue shift) in the peak positions (380, 398 nm) and emission of excimer (~440 nm) upon Hg$^{2+}$ ions addition. The fluorescence quenching, peak shifting, and excimer emission were attributed to the possible photoinduced electron transfer to the pyrene molecule and the formation of a stable Hg-pyrene complex with the emitting chromophore. It was observed that the presence of only a small amount of Hg$^{2+}$ ions (parts per billion (ppb) level) reduced the fluorescence intensity of pyrene up to a great extent (FIG. 11). The limit of detection (LOD) was estimated for Hg$^{2+}$ ions sensing, which is 3.3 times higher than the standard deviation of measurement. The results show that the developed fluorescent sensor may reliably quantify Hg$^{2+}$ ions ≥10 ppb (0.01 ppm) in aqueous environments.

Figure 12A:
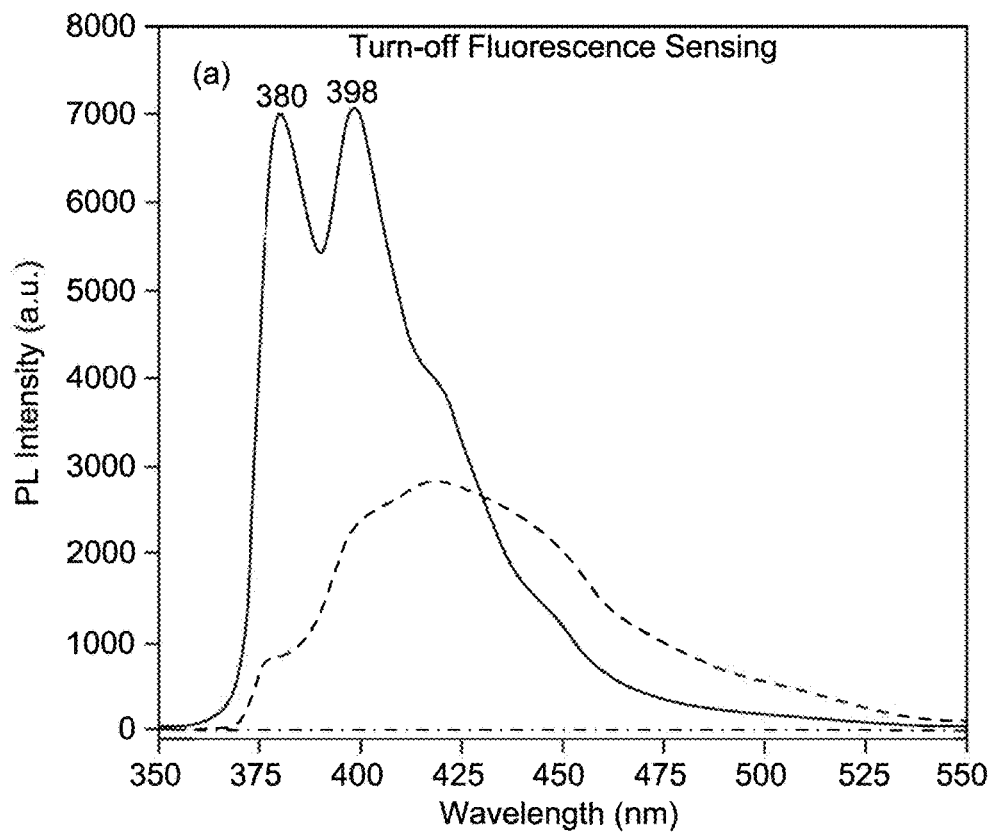
FIG. 12A illustrates PL emission spectra of real seawater (SW) samples which demonstrate fluorescence quenching of the Pyr-NH@SiO$_2$ NPs (20 ppm) upon addition of Hg$^{2+}$ ions (20 ppm); at $\lambda$ex=340 nm, according to certain embodiments.

The developed sensor was also tested to recognize Hg$^{2+}$ ions present in an accurate seawater sample. FIG. 12A demonstrates that the fluorescence intensity of Pyr-NH@SiO$_2$ NPs (20 ppm) quenches ~60% with the addition of spiked Hg$^{2+}$ ions (20 ppm) (1302). The results can be compared to the seawater sample with NH@SiO$_2$ NPs (20 ppm) without Hg$^{2+}$ ions (1304). This indicated the effective recognition of Hg$^{2+}$ ions in the presence of competitive metal cations in the seawater sample. To investigate the selectivity of the Pyr-NH@SiO$_2$ NPs sensor, the major cations of seawater such as Na$^+$, K$^+$, Ca$^{2+}$, Mg$^{2+}$, Ba$^{2+}$, and Ag$^+$ ions were individually analyzed with Pyr-NH@SiO$_2$ NPs, at a stoichiometric ratio of Hg$^{2+}$ ions with pyrene at 1:1 Therefore, the optimum concentration for each metal cation was kept at 20 ppm against Pyr-NH@SiO$_2$ NPs (20 ppm).

Figure 12B:
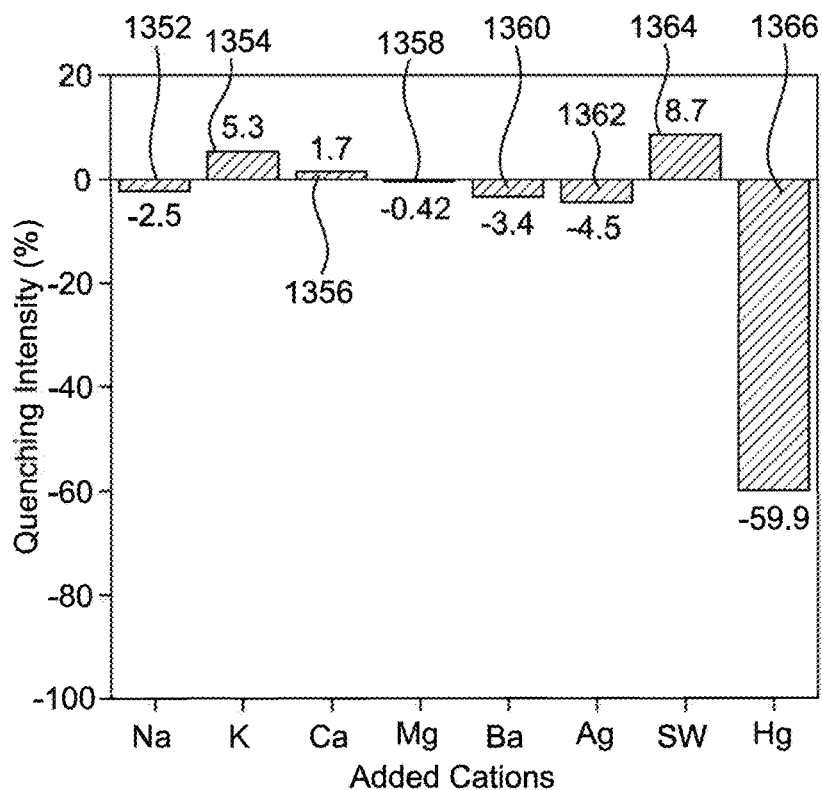
FIG. 12B illustrates a selectivity of the Pyr-NH@SiO$_2$ NPs against Hg$^{2+}$ ions upon the addition of major cations of seawater, according to certain embodiments

FIG. 12B demonstrates a slight change in the fluorescence intensity of Pyr-NH@SiO$_2$ NPs upon the addition of each competitive cation. The graph represents changes in the fluorescent intensity upon introduction of competitive cation as shown: Na$^+$ (1352), K$^+$ (1354), Ca$^{2+}$ (1356), Mg$^{2+}$ (1358), Ba$^{2+}$ (1360), Ag$^+$ (1362), and seawater, SW, (1364). A drastic quenching (~60%) of fluorescence intensity upon Hg$^{2+}$ (1366) addition, demonstrating the developed sensor's reliability and selectivity for seawater samples.

Pyrene attached silica nanoparticles (Pyr-NH@SiO$_2$ NPs) were successfully synthesized by the chemical attachment of pyrene with amino-functionalized silica NPs using peptide coupling agents. The chemical structure of amino-functionalized pyrene and its covalent attachment with silica NPs was confirmed by $^1$H-NMR, FT-IR, TGA, and BET results. The XRD results confirmed the amorphous nature of the synthesized silica NPs. Their average particle size was found to be ~40 nm. DLS outcomes indicate that Pyr-NH@SiO$_2$ NPs (38.0 mV) were stable in the aqueous environment after modification with 1-pyrene-carboxylic acid due to the formation of stable hydrogen bonding with water molecules in the presence of N—H and C=O groups. The synthesized fluorescent particles can produce bright green emission under UV light. The fluorescence quenching, hypochromic peak shifting (380, 398 nm), and excimer emission (~440 nm) upon adding $Hg^{2+}$ ions are attributed to the photoinduced electron transfer to the pyrene molecules and the formation of a stable Hg-pyrene complex with the emitting chromophore. The developed sensor can reliably and selectively recognize $Hg^{2+}$ ions (LOD: 10 ppb) in the presence of ubiquitous metal cations and seawater samples. The fluorescent Pyr-NH@SiO$_2$ NPs have great potential to design highly sensitive, selective, and portable opto-chemical mercury sensors for aqueous applications.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A method of detecting $Hg^{2+}$ ions in an aqueous solution, comprising:
    contacting the aqueous solution with a chemosensor to form a mixture; and
    monitoring a change in a fluorescence emission profile of the chemosensor in the mixture to determine a presence or absence of $Hg^{2+}$ ions in the aqueous solution;
    wherein the chemosensor comprises pyrene silica nanoparticles having at least one pyrene bonded to a surface of a silica nanoparticle through an amide bond with a formula of pyrene-C(=O)NHR-silica nanoparticle;
    wherein R is an alkyl chain.

2. The method of claim 1, wherein R is —CH$_2$CH$_2$CH$_2$—.

3. The method of claim 1, wherein the pyrene silica nanoparticles have a uniform size distribution; and an average size of 30-50 nm.

4. The method of claim 1, wherein the pyrene silica nanoparticles have a substantially spherical shape.

5. The method of claim 1, wherein the pyrene silica nanoparticles have an amorphous structure.

6. The method of claim 1, wherein the pyrene silica nanoparticles have a positively charged surface; and a zeta potential of 35-45 mV.

7. The method of claim 1, wherein the pyrene silica nanoparticles are agglomerated to form a mesoporous structure.

8. The method of claim 7, wherein the elements Si, O, C, and N are homogeneously distributed throughout the mesoporous structure.

9. The method of claim 1, wherein the pyrene silica nanoparticles have a BET surface area of 30-60 m$^2$/g.

10. The method of claim 1, wherein the pyrene silica nanoparticles have a total pore 15 volume of 0.25-0.4 cm$^3$/g.

11. The method of claim 1, wherein the pyrene silica nanoparticles have an average pore size of 20-30 nm.

12. The method of claim 1, wherein the pyrene silica nanoparticles are stable up to 200° C.

13. The method of claim 1, further comprising monitoring the change in the fluorescence emission profile of the chemosensor between 350-550 nm.

14. The method of claim 1, wherein the change in the fluorescence emission profile is measured by the disappearance of a fluorescence band from 360 to 425 nm.

15. The method of claim 1, wherein the change in the fluorescence emission profile is measured by the appearance of a fluorescence band from 400 to 525 nm.

16. The method of claim 1, wherein the change in the fluorescence emission profile linearly correlates with the concentration of $Hg^{2+}$ in the aqueous solution.

17. The method of claim 1, further comprising quantifying the change in the fluorescence emission profile to determine a concentration of $Hg^{2+}$ ions in the aqueous solution.

18. The method of claim 1, wherein the chemosensor is selective for detecting $Hg^{2+}$ ions.

19. The method of claim 1, wherein the aqueous solution further comprises at least one metal cation selected from the group consisting of Na$^+$, K$^+$, Ca$^{2+}$, Mg$^{2+}$, Ba$^{2+}$, and Ag$^+$; and
    the change in the fluorescence emission profile occurs only in the presence of $Hg^{2+}$.

20. The method of claim 1, wherein the limit of detection for $Hg^{2+}$ ions is 10 ppb.

* * * * *